United States Patent
Das et al.

(10) Patent No.: US 10,059,968 B2
(45) Date of Patent: Aug. 28, 2018

(54) METHOD FOR INCREASING LIPID CONTENT IN MICROORGANISMS AND MODIFIED MICROORGANISMS THEREFROM

(71) Applicant: Reliance Industries Limited, Mumbai (IN)

(72) Inventors: Gautam Das, Adilabad (IN); Santanu Dasgupta, Mumbai (IN); Venkatesh Prasad, Bangalore (IN); Vinodhkumar Vijayakumar, Batlagundu (IN); Pranali Deore, Panvel (IN); Kannadasan Kaliyamoorthy, Tamil Nadu (IN); Sujata Kumari, Bihar (IN)

(73) Assignee: RELIANCE INDUSTRIES LIMITED, Mumbai (IN)

( * ) Notice: Subject to any disclaimer, the term of this patent is extended or adjusted under 35 U.S.C. 154(b) by 0 days.

(21) Appl. No.: 15/314,227

(22) PCT Filed: May 28, 2015

(86) PCT No.: PCT/IB2015/054011
§ 371 (c)(1),
(2) Date: Nov. 28, 2016

(87) PCT Pub. No.: WO2015/181765
PCT Pub. Date: Dec. 3, 2015

(65) Prior Publication Data
US 2017/0342448 A1    Nov. 30, 2017

(30) Foreign Application Priority Data

May 29, 2014 (IN) .......................... 3757/MUM/2013

(51) Int. Cl.
| | | |
|---|---|---|
| C12N 1/12 | (2006.01) | |
| C12N 15/82 | (2006.01) | |
| C12P 7/64 | (2006.01) | |
| C12N 15/10 | (2006.01) | |
| C11C 3/00 | (2006.01) | |
| C12P 7/00 | (2006.01) | |

(52) U.S. Cl.
CPC .............. *C12P 7/6463* (2013.01); *C12N 1/12* (2013.01); *C12N 15/102* (2013.01); *C11C 3/00* (2013.01); *C12P 7/00* (2013.01)

(58) Field of Classification Search
CPC . C12P 7/6463; C12P 7/00; C12N 1/12; C12N 15/102; C11C 3/00
USPC .................. 435/257.1, 257.2, 257.6, 471
See application file for complete search history.

(56) References Cited

U.S. PATENT DOCUMENTS

2014/0004580 A1    1/2014 Roberts et al.
2017/0051293 A1    2/2017 Das et al.

FOREIGN PATENT DOCUMENTS

WO    2012087963 A1    6/2012
WO    20150181765 A1    12/2015

OTHER PUBLICATIONS

Coughlin et al., Prediction and verification of mouse tRNA gene families. RNA Biol., 2009, vol. 6(2): 1-8. (Year: 2009).*
Dastur et al., Analysis of the initiator tRNA genes from a slow- and a fast-growing mycobacterium. Arch. Microbiol., 2002, vol. 178: 228-296. (Year: 2002).*
Marck et al., tRNomics: Analysis of genes from 50 genomes of eukarya, archaea, and bacteria reveals anticodon-sparing strategies and domain-specific features. RNA, 2002, vol. 8: 1189-1232. (Year: 2002).*
Samhita et al., How many initiator genes does *Escherichia coli* need? J. Bacteriol. 201, vol. 196(14): 2607-2615. (Year: 2014).*
Ruffing, Anne M. et al., "Improved free fatty acid production in cyanobacteria with *Synechococcus* sp. PCC 7002 as host", Frontiers in Bioengineering and Biotechnology, 1-10, Original Research Article, dated May 26, 2014, 10 pages.
Kapoor, Suman et al., "Crucial contribution of the multiple copies of the initiator tRNA genes in the fidelity of tRNAfMet selection on the ribosomal P-site in *Escherichia coli*", 202-212 Nucleic Acids Research, 2011, vol. 39, No. 1, dated Aug. 26, 2010, 11 pages.
Søgaard Laursen, Brian et al., "Initiation of Protein Synthesis in Bacteria", Microbiology and Molecular Biology Reviews, vol. 59, No. 1, 101-123, dated Mar. 2005, 23 pages.
Ruffing, Anne M. et al., "Physiological effects of free fatty acid production in genetically engineered Synechococcus elongatus PCC 7942 as host", Frontiers in Bioengineering and Biotechnology, 2190-2199, dated May 26, 2014, 10 pages.
International Search Report and Written Opinion from PCT/IB2015/054011, dated Aug. 14, 2015, 11 pages.

* cited by examiner

*Primary Examiner* — Ganapathirama Raghu
(74) *Attorney, Agent, or Firm* — Westman, Champlin & Koehler, P.A.

(57) ABSTRACT

The present disclosure relates to a method for increasing lipid content in microorganisms. The method comprises decreasing the expression of molecules involved in the protein synthesis to decrease protein synthesis and thereby increase lipid synthesis in the microorganisms. The present disclosure also provides a modified microorganism having increased lipid content.

15 Claims, 5 Drawing Sheets

METHOD FOR INCREASING LIPID CONTENT IN MICROORGANISMS AND MODIFIED MICROORGANISMS THEREFROM

CROSS-REFERENCE TO RELATED APPLICATION

This Application is a Section 371 National Stage Application of International Application No. PCT/IB2015/054011, filed 28 May 2015 and published as WO 2015/181765 A1 on 3 Dec. 2015, in English, the contents of which are hereby incorporated by reference in their entirety.

FIELD

The present disclosure relates to a method for increasing the lipid content in microorganisms and modified microorganisms having increased lipid content therefrom.

BACKGROUND

Biofuels produced from living organisms such as plants and algae are alternative fuels to those derived from petroleum such as diesel and petrol. Algae are the preferred choice for producing biofuels as they are able to efficiently convert sunlight and carbon dioxide to biomass and synthesize lipids, and can grow in harsh environmental conditions. Many strains of algae produce triglycerides, which can be converted to biofuels.

Methods for increasing lipid content in microorganisms include nutrient-limitation, modulating enzyme activity, growing the microorganisms in a stress inducing environment and genetic engineering techniques. Though, these methods lead to an increase in lipid content, there is an overall decrease in the growth and cell-mass produced, which is undesirable.

It is known that a major amount of fixed carbon from photosynthesis is channeled to the production of proteins. Hence, decreased protein synthesis would lead to the utilization of this fixed carbon in making lipids, which can be used for the production of biofuels from the microorganisms, specifically from algae/cyanobacteria. The protein synthesis can be down-regulated and the carbon flux is redirected to the production of lipids.

Therefore, the inventors of the present disclosure envisage a method for decreasing the levels of protein synthesis in microorganisms whereby increased lipid content is obtained.

The disclosure also envisages modified strains of microorganisms such as algae and/or cyanobacteria having increased lipid content.

OBJECTS

Some of the objects of the present disclosure which at least one embodiment is adapted to provide, are described herein below:

It is an object of the present disclosure to provide a method for decreasing (down regulating) the expression of tRNA molecules involved in the protein synthesis to decrease protein synthesis and thereby increase lipid content in microorganisms.

It is another object of the present disclosure to provide a method for decreasing (down regulating) the rate of initiation process involved in the protein synthesis in microorganisms to decrease the levels of protein synthesis and thereby increase the lipid content in microorganisms.

It is still another object of the present disclosure to provide a method for decreasing the levels of protein synthesis in microorganisms to obtain increased lipid content leading to an increased overall productivity of biofuels.

It is yet another object of the present disclosure to provide modified strains of microorganisms having increased lipid content.

Other objects and advantages of the present disclosure will be more apparent from the following description when read in conjunction with the accompanying drawings, which is not intended to limit the scope of the present disclosure.

SUMMARY

The present disclosure in one aspect provides a method for increasing the lipid content in microorganisms. The method is characterized by the following steps: obtaining a knock-out gene construct for knocking out initiator tRNA gene; cloning the knock-out gene construct in a vector; introducing the vector containing the knock-out gene construct into a microorganism; and growing the microorganism on a medium containing a selective agent under conducive conditions and obtaining the microorganism with increased lipid content.

In another aspect of the present disclosure there is provided a modified strain of *Synechococcus elongatus* PCC 7942 having increased lipid content and having CCAP Accession Number 1479/17.

BRIEF DESCRIPTION OF THE ACCOMPANYING DRAWINGS

The method of the present disclosure will now be described with the help of the accompanying drawings, in which.

DETAILED DESCRIPTION

A major amount of fixed carbon from photosynthesis is channeled to the production of proteins. Hence, decreased protein synthesis would lead to utilization of this fixed carbon in making lipids, which can be used for the production of biofuels from the microorganisms, specifically from algae/cyanobacteria. The protein synthesis can be down-regulated and the carbon flux is redirected to the production of lipids.

It is observed that the initiator tRNA molecules or initiation factor proteins/ribosomal RNA present in microorganisms are responsible for initiation of protein synthesis. It is possible to decrease the amounts of cellular initiator tRNA molecules by genetic modification of the microorganisms so that the protein synthesis would be decreased.

Therefore, decreasing the availability of proteins by decreasing the rate of initiation of protein synthesis in microorganisms would lead to increased lipid content in the microorganisms. This would lead to increased biofuel production from these microorganisms.

Figure 1:
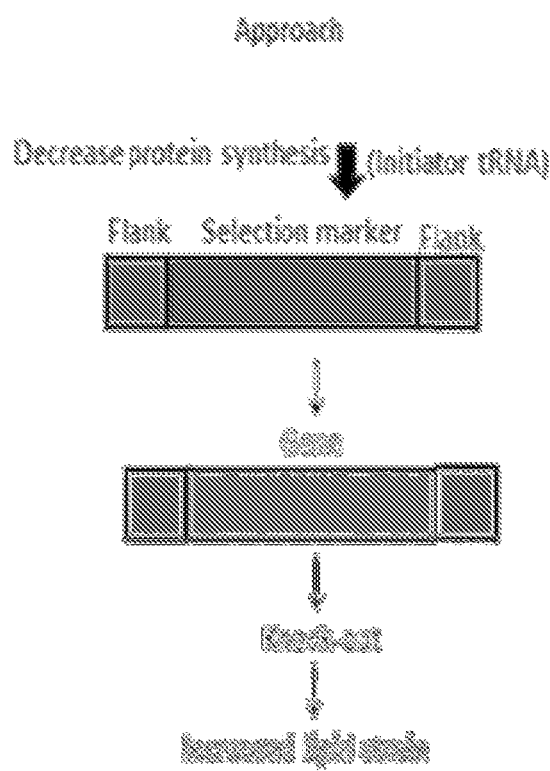
FIG. 1 illustrates a schematic process for increasing the lipid content in microorganisms by decreasing (down regulating) the protein synthesis in microorganisms.
Figure 2:
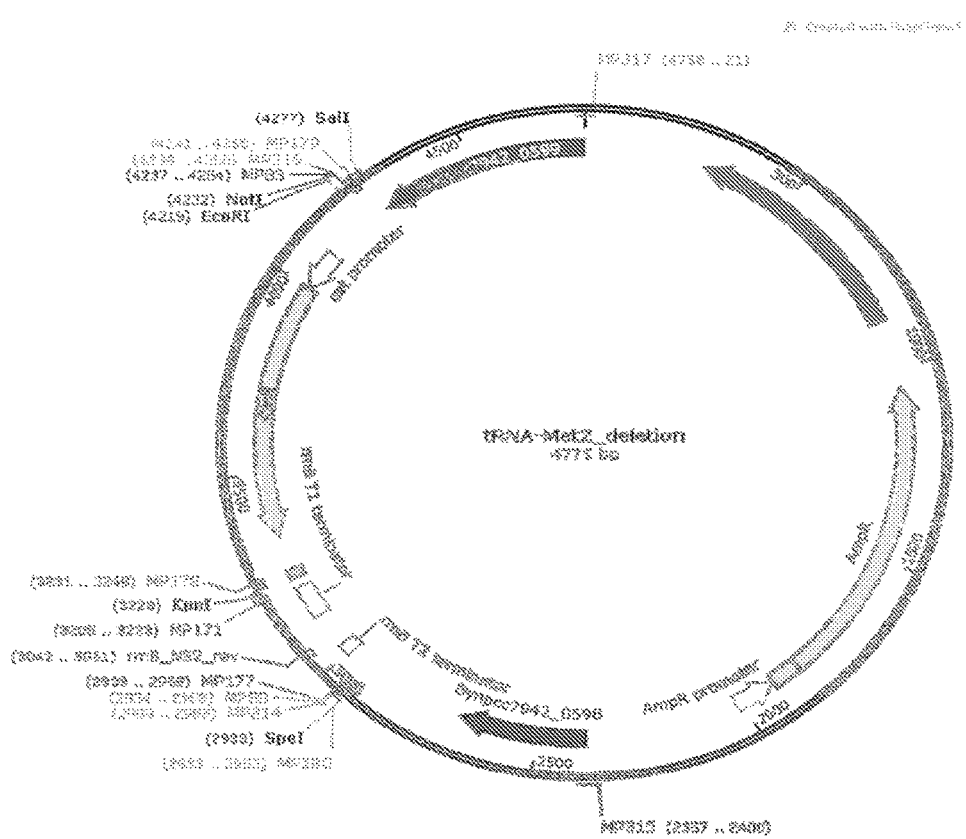
FIG. 2 illustrates the tRNA-Met2_deletion vector containing the knock-out gene construct prepared by deleting the initiator tRNA met2.

Therefore, in accordance with the present disclosure there is envisaged a method for decreasing (down regulating) protein synthesis in microorganisms, specifically in algae and cyanobacteria (as depicted in FIG. 1). The decrease in protein synthesis in the transformants would lead to utilization of the fixed carbon for the synthesis of lipid.

In an aspect of the present disclosure, there is provided a method for decreasing (down regulating) protein synthesis and thereby increasing the lipid content in microorganisms.

Figure 4A:
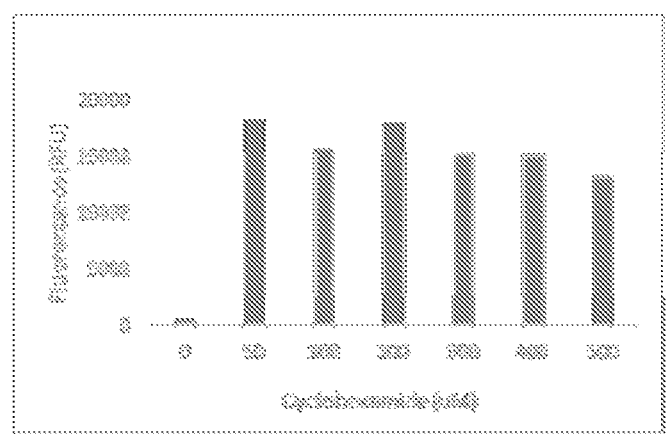
FIG. 4A illustrates the graphical representation of fluorescence observed for *Chlamydomonas reinhardtii* CW-15 cells (Day 4) in Tris Acetate Phosphate medium grown with and without cycloheximide using Nile Red Assay.
Figure 4B:
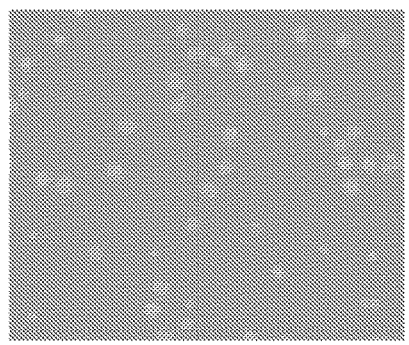
FIG. 4B illustrates Nile Red stained *Chlamydomonas reinhardtii* CW-15 cells grown in the absence of cycloheximide.
Figure 4C:
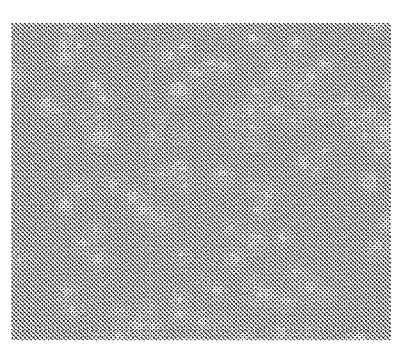
FIG. 4C illustrates Nile Red stained *Chlamydomonas reinhardtii* CW-15 cells grown in the presence of cycloheximide.

Chemical inhibition of protein synthesis is carried out using cycloheximide. *Chlamydomonas reinhardtii* CW-15 (Chlamydomonas Resource Center, USA), is grown in the presence of varying amounts of cycloheximide (50 µM to 500 µM) to find out the effect of inhibition of protein synthesis on lipid content. It is found that the chemical inhibition of protein synthesis results in an increase in lipid content (FIG. 4A). Highest lipid content is observed when the *Chlamydomonas reinhardtii* CW-15 cells are grown in the presence of 50 µM of cycloheximide. When higher amounts of cycloheximide (more than 200 µM) are used, a decrease in the lipid content is observed as illustrated in FIG. 4A. FIGS. 4B and 4C depict the Nile Red stained cells of *Chlamydomonas reinhardtii* CW-15 cells grown without the protein inhibitor and in the presence of the protein inhibitor, respectively. As seen from the FIG. 4C, an increase in the fluorescence is observed when the cells are grown in the presence of the protein inhibitor (cycloheximide), indicating an increase in the lipid content of the *Chlamydomonas reinhardtii* CW-15 cells as compared to the *Chlamydomonas reinhardtii* CW-15 cells grown in the absence of the protein inhibitor.

Transfer RNA Met1 and tRNA Met2 are two initiator tRNA genes present in cyanobacteria and both are involved in the regulation of protein synthesis. In accordance with the present disclosure, tRNA Met2 gene is knocked out. A knock-out gene construct in accordance with the present disclosure is prepared by taking out 1 kb flanking sequences of the initiator tRNA gene and cloning in a vector containing a selective marker. In an embodiment of the present disclosure the selective marker is an antibiotic selected from the group including but not limited to kanamycin, ampicillin and chloramphenicol.

In accordance with another aspect of the present disclosure, there are provided modified strains of microorganism, specifically modified strains of algae and/or cyanobacteria having increased lipid content, particularly, a modified strain in accordance with the present invention can be *Synechococcus elongatus* PCC 7942 deposited in the Culture Collection of Algae and Protozoa (CCAP), SAMS Limited, Scottish Marine Institute, Dunbeg, Oban, Argyll, PA37 1QA, UK and having CCAP Accession Number 1479/17.

The present disclosure is further described in light of the following laboratory experiments which are set forth for illustration purposes only and not to be construed for limiting the scope of the disclosure.

EXPERIMENT 1:

Transformation of *Synechococcus elongatus* Pcc 7942

One kilo base flanking sequences of the initiator tRNA (tRNA Met2) was taken out and then cloned into a vector containing an antibiotic (chloramphenicol) selection marker. The vector used in the present disclosure is tRNA-Met2_deletion. This vector was then used to knock-out the methionine tRNA (tRNA Met2) from *Synechococcus elongatus* PCC 7942.

*Synechococcus elongatus* PCC 7942 (Institut Pasteur, France) was inoculated into 50 ml of BG-11 Basal Solution (HiMedia) and allowed to grow overnight at 30° C. till an $OD_{730}$ of 1 (approximately $10^8$ cells/ml) was obtained. The culture was centrifuged at 4000 rpm and the pellet obtained was collected for further experiments.

The pellet was washed thrice with 10 ml of ice cold 1 mM 4-(2-hydroxyethyl)-1-piperazineethanesulfonic acid (HEPES) buffer having pH 7.5. The pellet was soaked in the HEPES buffer for 5 minutes during each washing step.

The supernatant was removed and the pellet was suspended in 500 µl of HEPES buffer containing 6% dimethyl sulfoxide (DMSO) and 10% glycerol and mixed properly by vortexing to obtain a cell mixture.

Hundred microliters of the above cell mixture was transferred into a pre-chilled Electroporation Cuvette. Five micro grams of linear DNA (dissolved in water) was added to the Electroporation Cuvette. One cuvette not having DNA was used as the control. The outside of the cuvette was completely dried and then placed in a Gene Pulser for electroporation. The electroporation parameters used in the present disclosure are given below:
i) Field strength 1800 V/cm
ii) Capacitance 25 µF
iii) Resistance 200Ω
iv) Exponential decay wave pulse After completion of electroporation, the cuvettes were immediately incubated in ice for 5 minutes. The cells were then suspended in 1 ml of BG-11 Basal Solution and then inoculated in an Erlenmeyer flask containing 20 ml of BG-11 Basal Solution. The cells were incubated for 5 days at 30° C. under white light.

Figure 5:
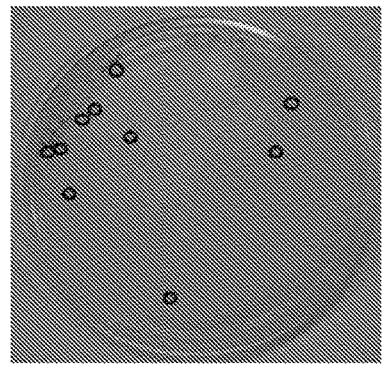
FIG. 5 illustrates the spot inoculation of *Synechococcus elongatus* PCC 7942 (with the tRNA Met2 gene knocked out) on a medium containing a selective agent.

After 5 days the cells were collected by centrifugation. The pellet obtained was suspended in 200 µl of BG-11 Basal Solution. The culture was inoculated on BG-11 Basal Solution containing 1% agar and chloramphenicol. Colonies were observed on the plates after 20 days (FIG. 5A). Single colony was further propagated in liquid and solid BG-11 medium containing chloramphenicol for 8 generations for homoplasmicity.

Figure 3:
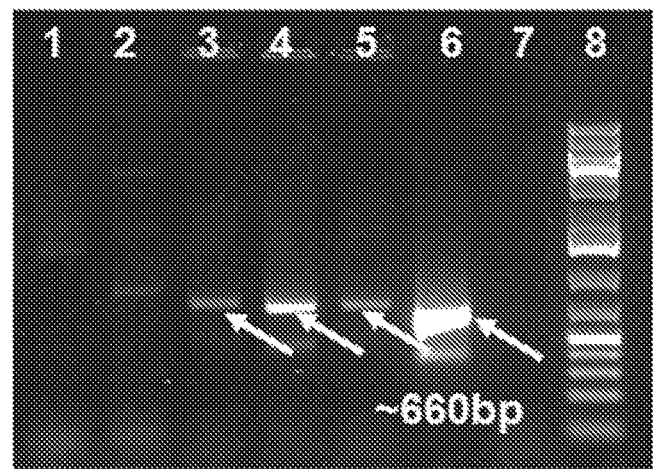
FIG. 3 illustrates the PCR confirmation of the transformants prepared in accordance with the present disclosure.

The transformation was confirmed by PCR using Chloramphenicol Acetyltransferase (CAT) gene primers as illustrated in FIG. 3. The DNA was isolated using Sigma plant DNA extraction kit and the genomic DNA was used as the template. From left to right: Lane-1 depicts the wild type, Lane-6 depicts the positive control containing pMet2 KO plasmid DNA, Lane-7 depicts the negative control without any DNA and Lane-8 depicts the 1 kb plus ladder marker (Thermo Scientific). Lane-2, Lane-3, Lane-4 and Lane-5 are the different transformants: Clone-1, Clone-3, Clone-4 and Clone-19, respectively prepared in accordance with the present disclosure. The vector tRNA-Met2_deletion has a size of 4775 bp. The arrow pointing to the band on Lane-6 (positive control), corresponds to 660 bp of the CAT gene. The wild type genomic DNA does not have a CAT gene and hence, no PCR product is observed after PCR and hence, there is no band corresponding to the wild type (Lane-1) as illustrated in FIG. 3. In the transformants, the tRNA Met2 gene was knocked-out and replaced with the CAT gene (660 bp). The arrows pointing to the bands in Lane-5 (Clone-19), Lane-4 (Clone-4) and Lane-3 (Clone-3) correspond to the CAT gene, confirming the transformation. The second band on Lane-2 is a non-specific band formed due to the PCR condition.

EXPERIMENT 2:

Comparison of the Lipid Produced by the Wild Type and the Transformants

Ten milligram of dry mass of the wild type and the transformants were used for performing GC analysis of Octadecanoic acid, methyl ester (C18:0) produced. The amount (in %) of C18:0 produced by the wild type and the transformants (Clone-3 and Clone-19) are given in FIG. 6 and Table-1.

Figure 6:
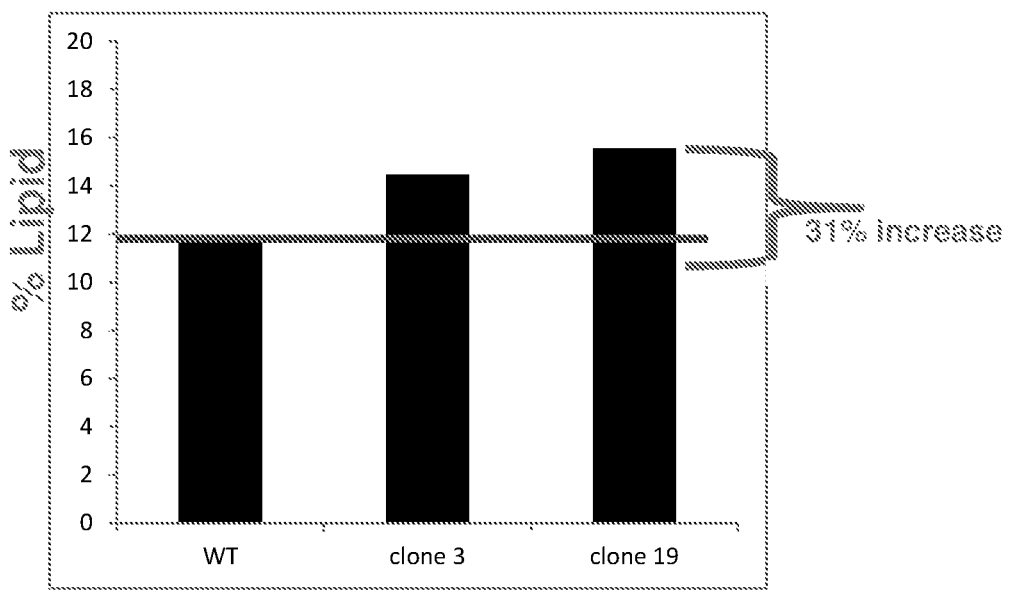
FIG. 6 depicts a graph illustrating the increase in lipid content in the modified strains of *Synechococcus elongatus* PCC 7942 as compared to the wild type.

Octadecanoic acid, methyl ester (C18:0) produced by the wild type and two transformants (Clone-3 and Clone-19) were compared as illustrated in FIG. 6. A 31% increase in the amount of lipid (C18:0) produced was observed for Clone-19 as compared to the wild type.

TABLE 1

| 10 mg of dry mass | % C18:0 |
|---|---|
| WT | 11.83 |
| Clone-3 | 14.47 |
| Clone-19 | 15.54 |

It is clear from FIG. 6 and Table-1 that the transformants (clone-3 and clone-19) show an increase in the lipid content as compared to the wild type, indicating that the down regulation of protein synthesis results in an overall increase of lipid content in the transformants.

Technical Advancements

The technical advancements offered by the present disclosure are as follows:

The present disclosure provides a method for decreasing (down regulating) the different molecules involved in protein synthesis to decrease the protein synthesis and hence, increase the lipid content of the microorganism.

The present disclosure provides a method for increasing the lipid content of microorganisms to obtain increased production of biofuels.

The present disclosure provides modified microorganisms with increased lipid content as compared to the wild type.

The embodiments as described herein above, and various features and advantageous details thereof are explained with reference to the non-limiting embodiments in the description. Descriptions of well-known aspects, components and molecular biology techniques are omitted so as to not unnecessarily obscure the embodiments herein.

The foregoing description of specific embodiments will so fully reveal the general nature of the embodiments herein, that others can, by applying current knowledge, readily modify and/or adapt for various applications of such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein. Further, it is to be distinctly understood that the foregoing descriptive matter is to be interpreted merely as illustrative of the disclosure and not as a limitation.

Having described and illustrated the principles of the present disclosure with reference to the described embodiments, it will be recognized that the described embodiments can be modified in arrangement and detail without departing from the scope of such principles.

While considerable emphasis has been placed herein on the particular features of this disclosure, it will be appreciated that various modifications can be made, and that many changes can be made in the preferred embodiment without departing from the principles of the disclosure. These and other modifications in the nature of the disclosure or the preferred embodiments will be apparent to those skilled in the art from the disclosure herein, whereby it is to be distinctly understood that the foregoing descriptive matter is to be interpreted merely as illustrative of the disclosure and not as a limitation.

The invention claimed is:

1. A method for increasing the lipid content in a photosynthetic microorganism, said method characterized by the following steps:
   a. obtaining a knock-out gene construct for inactivating initiator tRNA Met2 gene;
   b. cloning said knock-out gene construct in a vector comprising a selectable marker;
   c. introducing said vector containing the knock-out gene construct into a photosynthetic microorganism; and
   d. growing said photosynthetic microorganism under conducive conditions, wherein the conducive conditions comprise a medium containing the selectable marker and a pre-determined temperature for growth of the photosynthetic microorganism and obtaining said microorganism with increased lipid content.

2. The method as claimed in claim 1, wherein said photosynthetic microorganism is an alga.

3. The method as claimed in claim 2, wherein said alga, is *Chlamydomonas*.

4. The method as claimed in claim 1, wherein said knock-out gene construct comprises 1 kb flanking sequences of initiator tRNA Met2 gene.

5. The method as claimed in claim 1, wherein said vector is tRNA-Met2 deletion.

6. The method as claimed in claim 1, wherein said selective marker is at least one antibiotic selected from the group consisting of kanamycin, ampicillin and chloramphenicol.

7. A method for manufacturing a modified photosynthetic microorganism having increased lipid content, said method characterized by the following steps:
   a. obtaining a knock-out gene construct for inactivating initiator t RNA gene;
   b. cloning said knock-out gene construct in a vector;

c. introducing said vector containing the knock-out gene construct into a photosynthetic microorganism; and
d. growing said photosynthetic microorganism on a medium under conducive conditions, wherein the conducive conditions comprise a medium containing a selectable marker and a predeterimined temperature for growth of the photosynthetic microorganism to obtain the microorganism having increased lipid content, wherein the lipid content synthesized/produced by the modified microorganism is increased relative to the unmodified microorganism.

8. A modified photosynthetic microorganism manufactured by the method as claimed in claim 7.

9. The method as claimed in claim 7, wherein said photosynthetic microorganism with increased lipid content belongs to a strain of *Synechococcus elongatus* PCC 7942 having CCAP Accession Number 1479/17.

10. The method as claimed in claim 1, wherein said photosynthetic microorganism is cyanobacteria.

11. The method as claimed in claim 10, wherein the cyanobacteria is *Synechococcus*.

12. The method as claimed in claim 7, wherein said photosynthetic microorganism is an alga.

13. The method as claimed in claim 12, wherein said alga is *Chlamydomonas*.

14. The method as claimed in claim 7, wherein said photosynthetic microorganism is cyanobacteria.

15. The method as claimed in claim 14, wherein the cyanobacteria is *Synechococcus*.

* * * * *